(12) United States Patent
Richardson (10) Patent No.: US 8,979,870 B2
(45) Date of Patent: *Mar. 17, 2015

(54) DISTAL RELEASE RETRIEVAL ASSEMBLY AND RELATED METHODS OF USE

(71) Applicant: Boston Scientific Scimed, Inc., Maple Grove, MN (US)

(72) Inventor: Kevin Richardson, Austin, TX (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/047,704

(22) Filed: Oct. 7, 2013

(65) Prior Publication Data

US 2014/0025083 A1    Jan. 23, 2014

Related U.S. Application Data

(63) Continuation of application No. 13/366,892, filed on Feb. 6, 2012, now Pat. No. 8,551,111, which is a continuation of application No. 11/066,454, filed on Feb. 28, 2005, now Pat. No. 8,109,941.

(51) Int. Cl.
*A61B 17/22* (2006.01)
*A61B 17/221* (2006.01)
*A61B 17/3205* (2006.01)

(52) U.S. Cl.
CPC ......... *A61B 17/221* (2013.01); *A61B 17/32056* (2013.01); *A61B 2017/2212* (2013.01); *A61B 2017/2215* (2013.01)
USPC .......................................... 606/127; 606/113

(58) Field of Classification Search
USPC .................. 606/110, 113, 114, 127, 128, 200
See application file for complete search history.

(56) References Cited

U.S. PATENT DOCUMENTS

| 3,791,387 | A | * | 2/1974 | Itoh .............................. 606/113 |
| 4,611,594 | A | * | 9/1986 | Grayhack et al. ............. 606/127 |
| 5,011,488 | A | * | 4/1991 | Ginsburg ...................... 606/159 |
| 5,102,415 | A |   | 4/1992 | Guenther et al. |
| 5,190,542 | A | * | 3/1993 | Nakao et al. .................... 606/47 |
| 5,190,555 | A | * | 3/1993 | Wetter et al. .................. 606/114 |
| 5,192,284 | A | * | 3/1993 | Pleatman ...................... 606/114 |
| 5,192,286 | A | * | 3/1993 | Phan et al. .................... 606/127 |
| 5,201,740 | A | * | 4/1993 | Nakao et al. .................. 606/113 |
| 5,279,539 | A | * | 1/1994 | Bohan et al. ................... 600/37 |
| 5,320,602 | A |   | 6/1994 | Karpiel |
| 5,352,184 | A |   | 10/1994 | Goldberg et al. |
| 5,417,697 | A | * | 5/1995 | Wilk et al. .................... 606/113 |
| 5,486,182 | A | * | 1/1996 | Nakao et al. .................. 606/114 |
| 5,535,759 | A |   | 7/1996 | Wilk |
| 5,549,626 | A | * | 8/1996 | Miller et al. .................. 606/200 |
| 5,735,289 | A |   | 4/1998 | Pfeffer et al. |
| 5,741,271 | A | * | 4/1998 | Nakao et al. .................. 606/114 |
| 5,759,187 | A |   | 6/1998 | Nakao et al. |

(Continued)

*Primary Examiner* — Ryan Severson
(74) *Attorney, Agent, or Firm* — Seager, Tufte & Wickhem, LLC (57) ABSTRACT

A device and related method of use is provided for the capture and removal of various unwanted objects present within the body's anatomical lumens. In an embodiment of the present disclosure, the device includes an external elongate member; an internal elongate member disposed within the external elongate member; and a retrieval assembly connected to the internal elongate member and retractable within and extendable from a lumen of the external elongate member. The retrieval assembly includes an end configured to be selectively open or substantially closed.

16 Claims, 3 Drawing Sheets

(56) References Cited

U.S. PATENT DOCUMENTS

| | | | |
|---|---|---|---|
| 5,782,840 A * | 7/1998 | Nakao | 606/114 |
| 5,908,435 A * | 6/1999 | Samuels | 606/200 |
| 5,910,154 A * | 6/1999 | Tsugita et al. | 606/200 |
| 5,971,995 A * | 10/1999 | Rousseau | 606/114 |
| 5,997,547 A * | 12/1999 | Nakao et al. | 606/114 |
| 6,001,118 A | 12/1999 | Daniel et al. | |
| 6,010,522 A * | 1/2000 | Barbut et al. | 606/200 |
| 6,027,520 A * | 2/2000 | Tsugita et al. | 606/200 |
| 6,042,598 A * | 3/2000 | Tsugita et al. | 606/200 |
| 6,066,149 A | 5/2000 | Samson et al. | |
| 6,066,158 A | 5/2000 | Engelson et al. | |
| 6,096,053 A * | 8/2000 | Bates | 606/159 |
| 6,136,016 A * | 10/2000 | Barbut et al. | 606/200 |
| 6,146,396 A * | 11/2000 | Konya et al. | 606/159 |
| 6,159,220 A * | 12/2000 | Gobron et al. | 606/127 |
| 6,165,200 A * | 12/2000 | Tsugita et al. | 606/200 |
| 6,174,318 B1 * | 1/2001 | Bates et al. | 606/127 |
| 6,221,006 B1 | 4/2001 | Dubrul et al. | |
| 6,224,612 B1 * | 5/2001 | Bates et al. | 606/114 |
| 6,295,714 B1 | 10/2001 | Roychowdhury et al. | |
| 6,299,612 B1 * | 10/2001 | Ouchi | 606/47 |
| 6,302,895 B1 * | 10/2001 | Gobron et al. | 606/127 |
| 6,350,266 B1 * | 2/2002 | White et al. | 606/200 |
| 6,350,267 B1 * | 2/2002 | Stefanchik | 606/114 |
| 6,355,051 B1 * | 3/2002 | Sisskind et al. | 606/200 |
| 6,383,195 B1 | 5/2002 | Richard | |
| 6,395,014 B1 * | 5/2002 | Macoviak et al. | 606/200 |
| 6,458,139 B1 * | 10/2002 | Palmer et al. | 606/113 |
| 6,458,145 B1 * | 10/2002 | Ravenscroft et al. | 606/200 |
| 6,485,501 B1 * | 11/2002 | Green | 606/200 |
| 6,520,968 B2 | 2/2003 | Bates et al. | |
| 6,540,768 B1 | 4/2003 | Diaz et al. | |
| 6,610,077 B1 | 8/2003 | Hancock et al. | |
| 6,626,903 B2 * | 9/2003 | McGuckin et al. | 606/45 |
| 6,673,090 B2 * | 1/2004 | Root et al. | 606/200 |
| 6,695,858 B1 | 2/2004 | Dubrul et al. | |
| 6,695,865 B2 * | 2/2004 | Boyle et al. | 606/200 |
| 6,712,835 B2 * | 3/2004 | Mazzocchi et al. | 606/200 |
| 6,740,096 B2 | 5/2004 | Teague et al. | |
| 6,800,080 B1 * | 10/2004 | Bates | 606/127 |
| 6,824,545 B2 * | 11/2004 | Sepetka et al. | 606/113 |
| 7,063,707 B2 | 6/2006 | Bose et al. | |
| 8,109,941 B2 * | 2/2012 | Richardson | 606/127 |
| 8,551,111 B2 * | 10/2013 | Richardson | 606/127 |
| 2001/0031981 A1 * | 10/2001 | Evans et al. | 606/200 |
| 2001/0044632 A1 * | 11/2001 | Daniel et al. | 606/200 |
| 2002/0072764 A1 | 6/2002 | Sepetka et al. | |
| 2002/0138094 A1 * | 9/2002 | Borillo et al. | 606/200 |
| 2003/0229374 A1 * | 12/2003 | Brady et al. | 606/200 |
| 2003/0233099 A1 * | 12/2003 | Danaek et al. | 606/96 |
| 2004/0059345 A1 * | 3/2004 | Nakao et al. | 606/113 |
| 2004/0098025 A1 | 5/2004 | Sepetka et al. | |
| 2004/0098033 A1 * | 5/2004 | Leeflang et al. | 606/200 |
| 2005/0055034 A1 * | 3/2005 | Bates | 606/127 |
| 2005/0085808 A1 * | 4/2005 | Nakao | 606/47 |
| 2005/0154400 A1 * | 7/2005 | Kato et al. | 606/127 |
| 2005/0216031 A1 * | 9/2005 | White et al. | 606/114 |
| 2006/0047286 A1 * | 3/2006 | West | 606/114 |
| 2006/0129166 A1 * | 6/2006 | Lavelle | 606/113 |

\* cited by examiner

DISTAL RELEASE RETRIEVAL ASSEMBLY AND RELATED METHODS OF USE

RELATED APPLICATIONS

This application is a continuation of U.S. application Ser. No. 13/366,892, filed Feb. 6, 2012, now U.S. Pat. No. 8,551,111, which is a continuation of U.S. application Ser. No. 11/066,454, filed Feb. 28, 2005, now U.S. Pat. No. 8,109,941, the entire disclosures of which is incorporated herein by reference.

FIELD OF THE INVENTION

Embodiments of this invention relate generally to medical devices and procedures. In particular, embodiments of the instant invention relate to medical devices and procedures for assisting in the removal of tissue or foreign matter from a body portion.

BACKGROUND OF THE INVENTION

The biliary system delivers bile produced by the liver to the duodenum where the bile assists other gastric fluids in digesting food. The biliary system includes the liver, as well as a plurality of bodily channels and organs that are disposed between the liver and duodenum. When the liver produces bile, the bile enters biliary ducts that have relatively small cross-sectional areas, and that are dispersed throughout the liver. These biliary ducts carry the bile away from the liver and gradually merge with other biliary ducts. The last of the biliary ducts merge into the main biliary duct, from which the bile flows into the duodenum.

The biliary system also includes a gallbladder connected to one or more of the biliary ducts via the cystic duct. The gallbladder stores excess bile produced by the liver, and introduces the stored bile into the duodenum via the cystic duct and the biliary ducts when necessary.

Sometimes organic material (e.g., blood clots, tissue, and biological concretions such as urinary, biliary, and pancreatic stones) or inorganic material (e.g., components of a medical devices or other foreign matter) may obstruct or otherwise be present within the body's anatomical lumens, such as the biliary tree. For example, biological concretions can develop in certain parts of the body, such as kidneys, pancreas, and gallbladder. Minimally invasive medical procedures generally involve causing limited trauma to the tissues of the patient, and can be used to dispose of certain problematic biological concretions or similarly unwanted obstructions.

Lithotripsy and ureteroscopy, for example, may be used to treat biological concretions (e.g., kidney stones) in the body of patients. Lithotripsy is a medical procedure that uses energy in various forms, such as acoustic shock waves, pneumatic pulsation, electro-hydraulic shock waves, or laser beams, to pulverize biological concretions such as urinary calculi (e.g., kidney stones). The force of the energy, when applied either extracorporeally or intracorporeally, usually in focused and continuous or successive bursts, divides the concretion into smaller fragments that may be extracted from the body, or allowed to pass from the body, for example, through urination.

In certain instances, intracorporeal fragmentation of bodily concretions can become problematic if the stones or stone fragments, instead of progressing out of the patient's body, begin to migrate further into the body or towards an organ. In these circumstances, further medical intervention to prevent aggravation of the patient's condition may become necessary. Therefore, it may be desirable to be able to extract such fragments from the body using a single instrument, preventing the need for successive instrumentation which can cause greater trauma to the patient's tissue.

Accordingly, endoscopic procedures for treating abnormal pathologies within the alimentary canal system or biliary tree (including the biliary, hepatic, and pancreatic ducts) are increasing in number. Improvements in the quality of instrumentation have established endoscopy as a significant method of diagnosing and treating many pancreatic and biliary diseases. In general, for treatment of an abnormal pathology within a patient's body, an endoscope is first introduced into the body of the patient. The endoscope includes a proximal end and a distal end, and a lumen extending longitudinally therebetween. The endoscope may be guided through the patient's alimentary infrastructure until an opening at the distal end is proximate a desired location for gaining access to the area targeted for treatment. For example, treatment of the biliary tree may involve the distal end of the endoscope being positioned proximate the papilla of vater leading to the common bile duct and the pancreatic duct. At this point, the endoscope allows for components (e.g., catheters, stents, sphincterotomes, retrieval assemblies, and balloons) inserted through the lumen to access the targeted area and perform a desired operation.

Many stone extraction devices (e.g., stents, retrieval assemblies, and coiled medical extractions devices) can be used to entrap an object, such as a stone fragment, and drag it through an ampulla (i.e., a small dilatation in the patient's anatomical lumen) to remove it. However, occasionally an object may be too large to be extracted through an ampulla, or an obstacle is encountered upon forward movement of the stone fragment within the anatomical lumen. It may be necessary to provide further treatment, for example, lithotripsy or surgery.

Coiled medical extraction devices may also be used to prevent unwanted migration of stone fragments generated during a stone fragmentation procedure, and then safely and efficiently extract fragments from the patient's body. For example, during a lithotripsy procedure, a coiled medical extraction device can act as a backstop against any unwanted migration of stone fragments.

SUMMARY OF THE INVENTION

Embodiments of the invention provide a medical device and procedure that assists practitioners in the removal of tissue or foreign matter from a desired body portion by entrapment and releases the tissue or foreign matter from entrapment when desired.

In accordance with an aspect of the present disclosure, a medical device may include: an external elongate member having a proximal end, a distal end, and a lumen extending longitudinally between the proximal and distal ends; an internal elongate member extending within the lumen of the external elongate member and moveable relative to the external elongate member; a retrieval assembly connected to a distal end of the internal elongate member, retractable within and extendable from the lumen of the external elongate member, and having an end configured to be selectively open or substantially closed; and a flexible member integrated with the end of the retrieval assembly for substantially closing the end of the retrieval assembly.

In another aspect of the present disclosure, a medical device may include: an external elongate member having a proximal end, a distal end, and a lumen extending longitudinally between the proximal and distal ends; an internal elongate member extending within the lumen of the external elongate member and moveable relative to the external elongate member; and a retrieval assembly connected to a distal end of the internal elongate member, retractable within and extendable from the lumen of the external elongate member, and having an end configured to be selectively open or substantially closed, wherein the end configured to be selectively open or substantially closed is adapted to be selectively open when the retrieval assembly is expanded or substantially collapsed.

Various embodiments of the invention may include one or more of the following aspects: the end configured to be selectively open or substantially closed may comprise a distal end of the retrieval assembly; the device may further include an actuator having a proximal end actuable by a user for substantially closing or opening the end configured to be selectively open or substantially closed; the actuator may extend within a lumen of the internal elongate member; the flexible member may be interweaved with the end configured to be selectively open or substantially closed; the flexible member and actuator may comprise the same material; the flexible member and actuator may comprise a one-piece construction; the internal elongate member may be connected to a proximal end of the retrieval assembly; the retrieval assembly may further comprise a scaffolding having wires that cross each other at points, at least some of the wires may be connected at the points; at least some of the wires that cross each other may be unconnected at the points; the scaffolding may define a plurality of spaces between wires of the scaffolding; the retrieval assembly may be configured to be selectively expanded or substantially collapsed; the retrieval assembly may be configured to be substantially collapsed when retracted into the external elongate member; the end configured to be selectively open or substantially closed may be adapted to be selectively open when the retrieval assembly is expanded or substantially collapsed; the end configured to be selectively open or substantially closed may adapted to be substantially closed when the retrieval assembly is expanded or substantially collapsed; the internal elongate member may define a plurality of lumens; the plurality of lumens may include a first lumen accommodating an actuator for substantially closing or opening the end configured to be selectively open or substantially closed, and a second lumen, which may be configured to accommodate a guidewire.

A further aspect of the present disclosure includes a method of entrapping and removing an object from within a body. The method includes inserting a medical device into a body lumen, the medical device having an external elongate member having a proximal end, a distal end, and a lumen extending longitudinally between the proximal and distal ends, an internal elongate member extending within the lumen of the external elongate member, a retrieval assembly connected to a distal end of the internal elongate member and having an end configured to be selectively open or substantially closed, and a flexible member integrated with the end configured to be selectively open or substantially closed. The method further includes advancing the medical device to a desired body location, extending said internal elongate member and retrieval assembly distally relative to the external elongate member to deploy the retrieval assembly within a body lumen, entrapping the object within the retrieval assembly, and removing the medical device and entrapped object from within the body.

Various the embodiments of the invention may include one or more of the following aspects: the external elongate member may be retrieved proximally to deploy the retrieval assembly within a body lumen; the internal elongate member may define a plurality of lumens; the plurality of lumens may include a first lumen accommodating an actuator for substantially closing or opening the end configured to be selectively open or substantially closed, and a second lumen, which may be configured to accommodate a guidewire; the method may further comprise the step of substantially closing said end configured to be selectively open or substantially closed; the step of substantially closing the end configured to be selectively open or substantially closed may be performed after the retrieval assembly is deployed within a body lumen; the step of substantially closing the end configured to be selectively open or substantially closed may be performed prior to the step of deploying the retrieval assembly within a body lumen; the retrieval assembly may further comprise a scaffolding having wires that cross each other at points, at least some of the wires may be connected at the points; at least some of the wires that cross each other may be unconnected at the points; the scaffolding may define a plurality of spaces between the wires of the scaffolding; the end configured to be selectively open or substantially closed may comprise a distal end of the retrieval assembly; the flexible member may be interweaved with the end configured to be selectively open or substantially closed; the medical device may further include an actuator having a proximal end actuable by a user for substantially closing or opening the end configured to be selectively open or substantially closed; the method may further comprise the step of actuating the actuator to substantially close the end configured to be selectively open or substantially closed; the step of actuating the actuator to substantially close the end configured to be selectively open or substantially closed may be performed before the retrieval assembly is deployed within a body lumen; the step of actuating the actuator to substantially close the end configured to be selectively open or substantially closed may be performed after the retrieval assembly is deployed within a body lumen; the method may further comprise the step of manipulating the actuator to open the end configured to be selectively open or substantially closed; the step of manipulating the actuator to open the end configured to be selectively open or substantially closed may be performed prior to removing the medical device from within a body; the method may further comprise releasing the object from the retrieval assembly after opening the end configured to be selectively open or substantially closed; the internal elongate member may be connected to a proximal end of the retrieval assembly; the retrieval assembly may be configured to be selectively expanded or substantially collapsed; the method further comprising the step of expanding the retrieval assembly; the step of expanding the retrieval assembly may be performed prior to the step of entrapping the object within the retrieval assembly; the retrieval assembly may be configured to be selectively expanded or substantially collapsed; the step of substantially closing the end configured to be selectively open or substantially closed may be performed prior to step of expanding the retrieval assembly; the step of substantially closing the end configured to be selectively open or substantially closed may be performed after the step of expanding the retrieval assembly; the step of manipulating the actuator to open the end configured to be selectively open or substantially closed may be performed prior to step of expanding the retrieval assembly; the step of manipulating the actuator to open the end configured to be selectively open or substantially closed may be performed after the step of expanding the retrieval assembly.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to embodiments of the invention, an example of which is illustrated in the accompanying drawings. Wherever possible, the same reference numbers will be used throughout the drawings to refer to the same or like parts.

Figure 1:
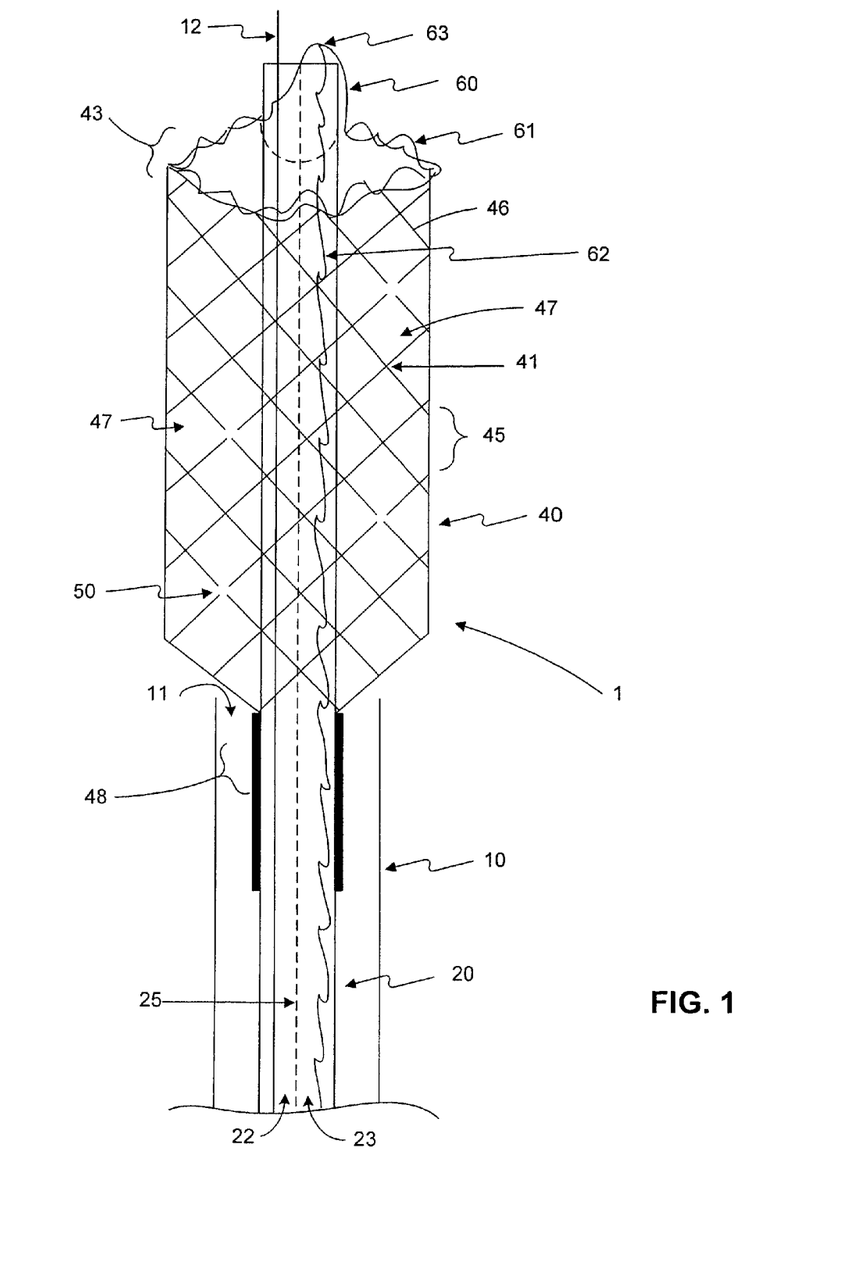
FIG. 1 is a schematic view of a medical device in an expanded state and having a selectively closeable distal end in an open configuration, according to an embodiment of the present disclosure
Figure 2:
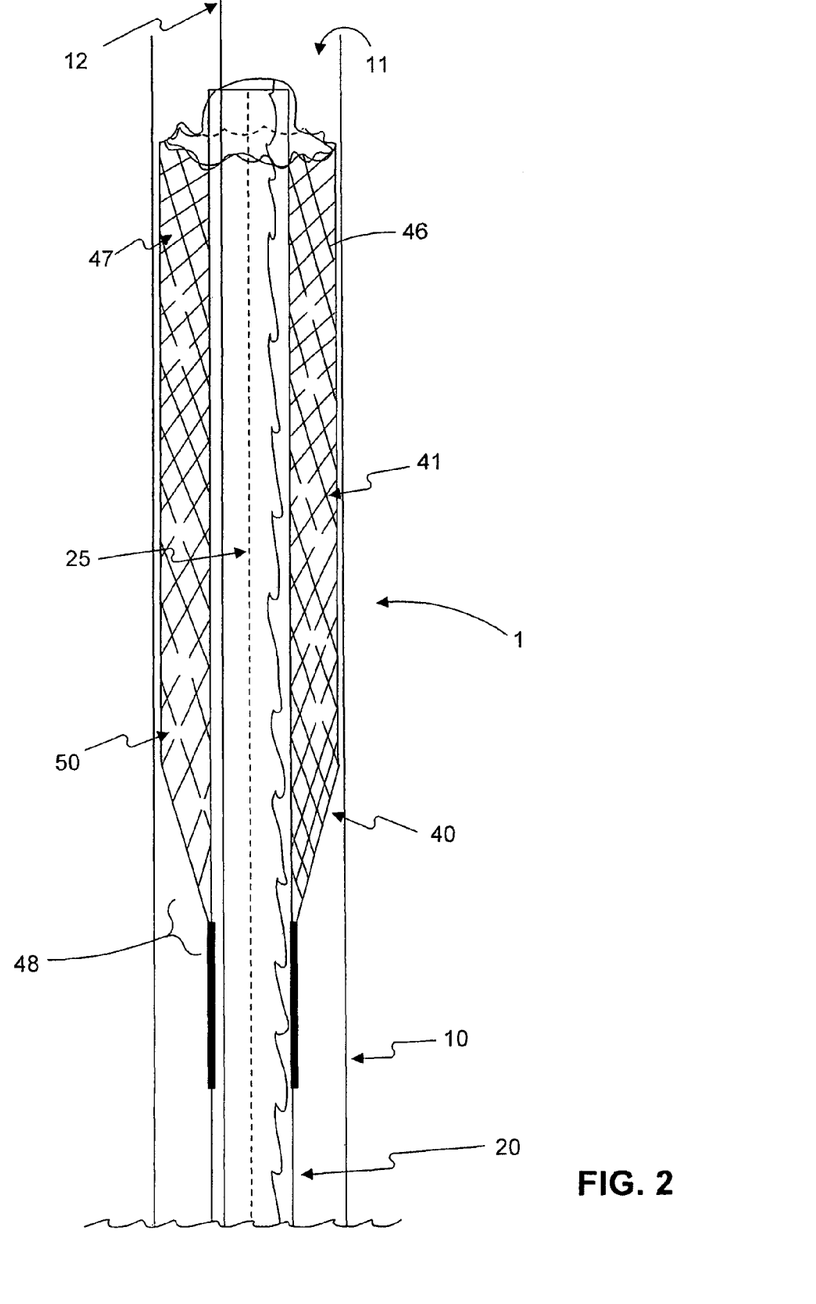
FIG. 2 is a schematic view of the device in FIG. 1 in a collapsed state.
Figure 3:
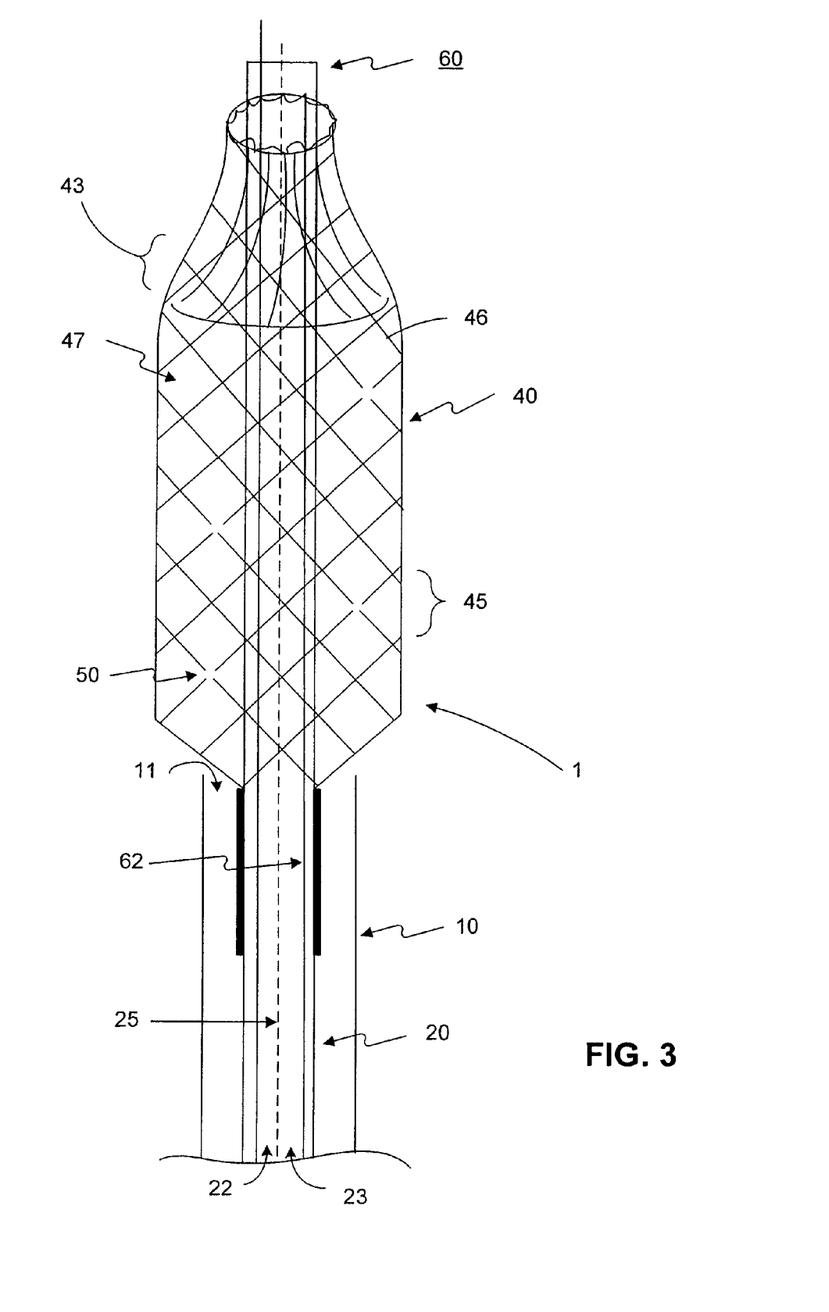
FIG. 3 is a schematic view of the device in FIG. 1 in an expanded state and with its distal end in a closed configuration.

FIGS. 1-3 depict certain configurations of an exemplary embodiment of a medical device 1. The medical device 1 includes an external elongate member 10, an internal elongate member 20, and a distal retrieval assembly 40. As used in this disclosure, "distal" refers to a position or direction furthest from a user of the device and "proximal" refers to a position or direction opposite "distal" and closest to the user.

External elongate member 10 may be any suitable sheath or catheter known in the art. External elongate member 10 may be fabricated by any known process such as, for example, extrusion. In addition, external elongate member 10 may be made from any suitable material. Such materials may include, but are not limited to, polyurethane and/or silicone. External elongate member 10 may have any desired cross-sectional shape and/or configuration. For example, external elongate member 10 may have a substantially circular cross-section. The external elongate member 10 may also have one or more cross-sectional shapes and/or configurations along its length, and may be any desired dimension suitable for deployment within a desired body lumen. For example, external elongate member 10 may have dimensions adapted for placement in a biliary duct having a particular size. For instance, the external elongate member 10 may have an outer periphery that is substantially the same size as the inner periphery of the biliary duct having a particular size. The overall length and diameter of the external elongate member 10 may vary depending on the application. For example, a relatively long external elongate member 10 may be advantageous for retrieving stones or other concretions deep within the body of a patient. Furthermore, external elongate member 10 may also be flexible along at least a portion of its length so that it may bend as it is advanced through tortuous body lumens.

External elongate member 10 may further include at least one lumen 11 extending therethrough. In some embodiments, lumen 11 may be defined as an internal passageway with an entrance and an exit, and may be formed by any suitable process such as, for example, extrusion. Alternatively, the external elongate member 10 may include a plurality of lumens (not shown) that may or may not differ in size. In such embodiments, the plurality of lumens may provide passageways useful in delivering, or removing, for example, medical devices, fluids, and/or other structures to or from a treatment site. The lumen 11 provided within member 10 may have any cross-sectional shape, dimension, and/or configuration. For example, in some embodiments lumen 11 may have a substantially circular cross-section.

Internal elongate member 20 extends within lumen 11 of the external elongate member 10, and may be configured to move longitudinally relative to the external elongate member 10. Internal elongate member 20 may be any suitable sheath or catheter known in the art. Internal elongate member 20 may be fabricated by any known process such as, for example, extrusion. In addition, internal elongate member 20 may be made from any suitable material. Such materials may include, but are not limited to, polyurethane and/or silicone. Furthermore, internal elongate member 20 may have any desired cross-sectional shape and/or configuration. For example, internal elongate member 20 may have a substantially circular cross-section. In addition, the internal elongate member 20 may also have one or more cross-sectional shapes and/or configurations along its length, and may have any desired dimension suitable for deployment in a desired body lumen, and retraction into elongate member 10. For example, the elongate member 20 may have an outer periphery that facilitates insertion into elongate member 10, and permits longitudinal movement of internal elongate member 20 relative to external elongate member 10. The overall length and diameter of the internal elongate member 20 may vary depending on the application. For example, a relatively small diameter may be advantageous for retrieving stones or other concretions from restricted passageways within the human urinary tract. Furthermore, internal elongate member 20 may also be flexible along at least a portion of its length so that it may bend as it is advanced through tortuous body lumens.

Internal elongate member 20 may further include two lumens 22 and 23. The lumens 22 and 23 may be approximately the same size, or alternatively, they may differ in size. In some embodiments, the lumens 22 and 23 may be separated by an internal wall 25, and may be defined as internal passageways with entrances and exits. Wall 25 may be fabricated from any suitable material and may be perforated or non-perforated. The lumens 22 and 23 may comprise any cross-sectional shape, dimension, and/or configuration. For example, in embodiments where wall 25 separates the lumens, the lumens may have a substantially semi-circular shape. Alternatively, the internal elongate member 20 may only include a single lumen (not shown) defined as an internal passageway with an entrance and an exit. Lumens 22 and 23 or any other lumen provided may be formed by any suitable process such as, for example, extrusion.

The retrieval assembly 40 includes wire-like scaffolding 45 manufactured out of any material suitable for self-expansion, for example, one or more metals and/or composites, such as, but not limited to, stainless steel or nitinol. The retrieval assembly 40 may have any desired cross-sectional shape and/or configuration. For example, the retrieval assembly 40 may have a substantially circular cross-section. The retrieval assembly 40 may also have one or more cross-sectional shapes and/or configurations along its length, and any desired dimensions suitable for deployment in a desired body lumen. For example, retrieval assembly 40 may have dimensions adapted for placement in a biliary duct having a particular size. For instance, the retrieval assembly 40, in an expanded state, may have an outer periphery that is substantially the same size as the inner periphery of the biliary duct having a particular size. In addition, the retrieval assembly 40 may have a configuration or dimensions, or have material properties, that permit longitudinal movement of the retrieval assembly 40 relative to the external elongate member 10 and extension and retraction into and out of the external elongate member 10. The overall length and diameter of the retrieval assembly 40 may vary depending on the application. For example, a relatively small diameter may be advantageous for retrieving stones or other concretions from restricted passageways within the human urinary tract. The retrieval assembly 40 may also be collapsible so that it may be more easily advanced through body lumens in its collapsed state, and, when desired, self-expandable for deployment.

The wire-like scaffolding 45 may be a stent or stent-like device composed of a plurality of wires 46 having any desired pattern, configuration, and characteristic suitable for entrapping objects within an anatomical lumen. For example, as shown in FIGS. 1-3, the wires 46 may have a substantially criss-cross configuration, with the wires 46 being unconnected at some of the cross-points 50 and connected at other cross-points 41. One exemplary advantage to using a stent or stent-like device having wires connected at some cross-points 41 and unconnected at other cross-points 50, is that such a configuration has fewer connections and therefore greater open areas to facilitate entrapment of objects.

Scaffolding 45 may define a plurality of cells or spaces 47 between the wires 46. The spaces 47 may be of any suitable shape, size, and/or configuration. The spaces 47, along with the unconnected wires 46 at cross-points 50, for example, may be configured to accommodate and allow objects to pass into the interior of the retrieval assembly 40 for entrapment and subsequent removal from the body.

Additionally, the retrieval assembly 40 may comprise a selectively open or closed distal end 43. In the embodiment shown, closing of the distal end 43 is accomplished through the use of a closure mechanism 60. Closure mechanism 60 includes suture or other similar flexible material 61 surrounding the distal end 43 of assembly 40 and joined to wires 46 at the distal end 43. The joining of material 61 to wires 46 may be through a loose interweaving of material 61 within spaces 47 at the distal end of the scaffolding 45. However, any other suitable means of joining material 61 to retrieval assembly 40 may also be used.

User selected actuation of closure mechanism 60 to close distal end 43 may be achieved through an actuator 62. The actuator 62 may be a flexible material such as suture or wire, or a rigid mechanical linkage, having proximal and distal ends. The actuator 62 may be provided in a lumen of the internal elongate member 20, such as lumen 23, and accessible to a user at the proximal end of lumen 23. Actuator 62 and material 61 may be fabricated from the same material and comprise a one-piece construction. Alternatively, actuator 62 may be made of a different material from that of material 61 and attached to material 61 at connection 63. Connection 63 of actuator 62 to material 61 may be accomplished through any suitable means, such as welding, tying, adhesives, etc. In embodiments where a closure mechanism 60 is provided, one method of closing the distal end 43 may be accomplished by applying a pulling force to the actuator 62 in the proximal direction. Pulling actuator 62 proximally places material 61 in tension so that it operates as a cinching mechanism and cinches around the wires 46 in a manner that closes the distal end 43 of the retrieval assembly 40.

The distal end 43 of the retrieval assembly 40 may be selectively returned to an open configuration by manipulating actuator 62 to remove the pulling force applied to the actuator 62. Because the retrieval assembly may be made of a resilient material suitable for self-expansion, or a shape (e.g., cylindrical) that possesses outwardly acting radial forces, removing the pulling force applied to the actuator 62 removes the tensile forces applied to material 61 and allows the distal end 43 to resiliently return to an open configuration.

The retrieval assembly 40, shown and described in FIGS. 1-3, is an exemplary retrieval assembly that may be used in the method and device of the present invention. Any other suitable retrieval assembly capable of entrapping, releasing, and/or removing objects from within a body lumen may be used.

Proximal end 48 of retrieval assembly 40 may be connected to a region of the internal elongate member 20, such as the distal end of internal elongate member 20, through any suitable connection means. Connection of the proximal end 48 to the internal elongate member 20 may be accomplished through any suitable means of fixedly connecting retrieval assembly 40 to internal elongate member 20. For example, possible connections may include, but are not limited to, welding, soldering, and/or crimping.

As shown in FIGS. 1-2, the retrieval assembly 40 may be configured to collapse and expand as desired. For example, the retrieval assembly 40 may be configured to be collapsible such that it facilitates refraction into lumen 11 of the external elongate member 10 as shown in FIG. 2, and/or advanced out of external elongate member 10, such that the retrieval assembly at least partially expands and/or fully expands as shown in FIG. 1. In such an example, the retrieval assembly 40 may be collapsed and retracted into lumen 11 of the external elongate member 10, while the external elongate member 10 is being advanced through a body lumen to a desired body location. Once the elongate member 10 is positioned at the desired body location, the retrieval assembly 40 may be advanced out of the external elongate member 10 for expansion.

The retrieval assembly 40 may be retracted into and/or advanced out of lumen 11 of the external elongate member 10 using any method known in the art. For example, by means of the connection between proximal end 48 and the internal elongate member 20, movement of the internal elongate member 20 relative to the external elongate member 10 causes the retrieval assembly 40 to also move relative to the external elongate member 10, allowing the retrieval assembly to be retracted into and/or advanced out of the elongate member 10. Any suitable known handle assemblies may be used at the proximal user end for actuation.

In reference to FIGS. 1-3, embodiments of the invention may include methods of using the medical device 1 of the present disclosure to retrieve stones and other unwanted materials located in the bladder, ureter, kidney, or other body structures. Medical device 1 may be used in an environment that is relatively fluid filled or that is relatively dry. The medical device 1 may be inserted through the urethra of a patient or, alternatively, the medical device 1 may be inserted percutaneously. The medical device 1 may be used in any location of the body in which a passageway or orifice includes unwanted material to be removed and/or is being at least partially blocked.

The medical device 1 may be advanced to a treatment site in a number of different ways. For example, the device 1 may be advanced to a desired body location over a guidewire 12, wherein the desired body location may correspond to the vicinity of a stone, or another object targeted for removal. The medical device 1 may also be advanced to the treatment site through an access sheath or any other access device known in the art.

Alternatively, the medical device 1 may be fed to the desired body location by means of an imaging device, and may travel through the body without the use of a guidewire or access sheath. To facilitate such feeding, the external elongate member 10 may include radiopaque marker bands (not shown) detectable by x-ray or other imaging means. Thus, the user may monitor the position of the device 1 and movement thereof through the use of an imaging device.

As yet another alternative, the device 1 may be used in conjunction with an endoscope (not shown) or any other type of intracorporeal scope known in the art. The endoscope may travel through the body to the treatment site in any conventional manner. Once the endoscope is positioned adjacent to the treatment site, the medical device 1 may be fed through an access port of the endoscope to gain access to the object targeted for removal, such as a stone.

Although not shown, the object targeted for retrieval may be a bodily concretion such as, for example, a stone. The object targeted for retrieval may include, but is not limited to, kidney stones, gallbladder stones, uric acid stones, or other solids commonly removed from a body structure or passageway. The objects may be of any size and/or shape. Furthermore, the medical device 1 may be used to retrieve objects that are both impacted and free floating.

In clinical applications where a guidewire 12 is used for access, the guidewire 12 may be advanced through a tortuous body lumen and past a desired body location. The medical device 1 then may be inserted into the body lumen by inserting lumen 22 of the internal elongate member 20 over guidewire 12. With the retrieval assembly 40 disposed inside of the external elongate member 10 and in a collapsed and retracted state, the medical device 1 then may be advanced over the guidewire 12 through a body lumen to a desired body location. For example, the medical device 1 may be advanced until the distal end of the external elongate member 10 has reached a desired location, such as, a short distance past an object targeted for entrapment and removal. The method is not limited to use with any particular object, and may also be used with one or more intracorporeal and/or extracorporeal objects at various locations and of various geometries and compositions.

Once the distal end of the external elongate member 10 is advanced past a targeted object, the internal elongate member 20 may then be advanced distally out of external elongate member 10, so that the retrieval assembly 40 self expands. This may be achieved by pulling member 10 proximally relative to member 20. When fully deployed, the retrieval assembly 40 may be substantially cylindrically shaped or have any other configuration suitable to the particular size and shape of both the targeted object and/or the environment it is located in. The proximal end 48 of the retrieval assembly 40 may remain in a collapsed state and/or disposed within the external elongate member 10, and may be the narrowest portion of the retrieval assembly 40. Alternatively, proximal end 48 may extend out of the distal end of external elongate member 10.

Once the internal elongate member 20 has been sufficiently advanced out of the external elongate member 10 to allow at least partial deployment and/or expansion of retrieval assembly 40, the proximal end of the actuator 62 of closure mechanism 60 may be actuated such that the distal end of the retrieval assembly is closed. This may be achieved by applying a pulling force to actuator 62 in the proximal direction relative to the retrieval assembly 40. This causes material 61 to cinch around wires 46 at distal end 43 of assembly 40 to close distal end 43. The medical device 1 may then be moved proximally, and sometimes repeatedly, such that the object targeted for entrapment passes through spaces 47 and becomes entrapped within retrieval assembly 40.

In certain embodiments, the steps related to entrapping the targeted object may be completed before the closure mechanism 60 is actuated to close the distal end 43 of retrieval assembly 40. In other embodiments, the retrieval assembly 40 may be deployed into the body with its distal end 43 already in the closed configuration. Consequently, the retrieval assembly 40 also then may be deployed to its expanded state while the distal end 43 remains in the closed configuration, as shown in FIG. 3.

The medical device 1, along with the entrapped object, may then be moved to any desired location, or may be allowed to remain stationary. For example, the medical device 1 may be used as an extraction device and removed from the body, assist in immobilizing objects and used as a backstop, or moved to a location more conducive to any additional procedures, such as lithotripsy, surgery, or any other processes known in the art.

In certain circumstances, it may be desired to release the entrapped object after it has been captured in the retrieval assembly 40. To do so, the closure mechanism 60 may be actuated to open the distal end 43 and allow the entrapped object to be released. For example, this may be accomplished by opening the distal end 43 of retrieval assembly 40 and retracting the medical device 1 in the proximal direction, allowing the entrapped object to exit through the opened distal end 43.

The distal end 43 of the retrieval assembly 40 may be opened by manipulating the actuator 62 to remove the pulling force imparted upon actuator 62 so that the distal end 43 may resiliency return to an open configuration, and allow the entrapped object to be released.

If desired, the closure mechanism 60 may again be actuated to close the distal end 43, such that another targeted object may become entrapped within the retrieval assembly 40. Furthermore, the medical device 1 may also be re-used with the same patient, for example, by retracting the inner elongate member 20 and recollapsing the retrieval assembly 40 within the external elongate member 10 and repositioning or reinserting the medical device 1 in the body.

By way of example, one advantage of using the retrieval assembly 40 with a selectively open or closed distal end 43 is that in cases where the entrapped object may be too large for successful removal from the body, the object may be released and the medical device 1 may be safely removed from the body.

Embodiments of the invention may be used in any medical or non-medical procedure, including any medical procedure where removal of an object from within a body lumen is desired. In addition, at least certain aspects of the aforementioned embodiments may be combined with other aspects of the embodiments, or removed, without departing from the scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
    an outer elongate member having a proximal end, a distal end, and a lumen extending therebetween;
    an inner elongate member disposed within the lumen of the outer elongate member, the inner elongate member having a proximal end region and a distal end region;

an expandable scaffold having a proximal end secured to an outer surface of the distal end region of the inner elongate member and a distal end capable of being actuated between a substantially open and a substantially closed configuration, the scaffold comprising a plurality of wires that cross each other at points and wherein at least some of the wires are connected at the points and at least some of the wires are unconnected at the points; and an actuator extending through a lumen of the inner elongate member, the actuator configured to move the expandable scaffold between the substantially open and substantially closed configurations.

2. The medical device of claim 1, wherein the actuator is affixed to the expandable scaffold proximate the distal end of the expandable scaffold.

3. The medical device of claim 1, wherein the inner elongate member is slidably disposed within the outer elongate member.

4. The medical device of claim 3, wherein the scaffold is configured to be substantially collapsed when retracted within the outer elongate member.

5. The medical device of claim 4, wherein the scaffold is configured to self-expand when extended distally beyond the lumen of the outer elongate member.

6. The medical device of claim 1, wherein the actuator includes a flexible member interwoven into the distal end of the scaffold.

7. The medical device of claim 1, wherein the scaffold remains secured to the inner elongate member while the scaffold is actuated between the substantially open and substantially closed configurations.

8. The medical device of claim 1, wherein the actuator extends through a lumen of the inner elongate member and exits from a distal terminal end of the inner elongate member, wherein a proximal end of the actuator is actuable by a user for substantially closing or opening the distal end of the scaffold.

9. A medical device comprising:
an outer elongate member having a proximal end, a distal end, and a lumen extending therebetween;
an inner elongate member disposed within the lumen of the outer elongate member, the inner elongate member having a proximal end region, a distal end region, and a distal terminal end;
an expandable scaffold comprising a plurality of wires that cross each other at points, the scaffold extending around the inner elongate member and having a proximal end and a distal end, wherein the proximal end of the scaffold is secured to an outer surface of the distal end region of the inner elongate member and the distal end of the scaffold is capable of being actuated between a substantially open and a substantially closed configuration and at least some of the wires are connected at the points and at least some of the wires are unconnected at the points; and an actuator extending through the inner elongate member and exiting from the distal terminal end of the inner elongate member, the actuator configured to move the expandable scaffold between the substantially open and substantially closed configurations.

10. The medical device of claim 9, wherein the actuator is affixed to the expandable scaffold proximate the distal end of the expandable scaffold.

11. The medical device of claim 9, wherein the inner elongate member is slidably disposed within the outer elongate member.

12. The medical device of claim 11, wherein the scaffold is configured to be substantially collapsed when retracted within the outer elongate member.

13. The medical device of claim 12, wherein the scaffold is configured to self-expand when extended beyond the lumen of the outer elongate member.

14. The medical device of claim 9, wherein the actuator includes a flexible member interwoven into the distal end of the scaffold.

15. The medical device of claim 9, wherein the scaffold remains secured to the inner elongate member while the scaffold is actuated between the substantially open and substantially closed configurations.

16. The medical device of claim 9, wherein a distal end of the lumen of the outer elongate member has a cross-sectional size smaller than a cross-sectional size of the scaffold when expanded.

* * * * *